United States Patent
Merrell

(10) Patent No.: US 9,622,798 B2
(45) Date of Patent: Apr. 18, 2017

(54) INTRAMEDULLARY COMPRESSION ROD

(76) Inventor: Gregory Merrell, Indianapolis, IN (US)

( * ) Notice: Subject to any disclaimer, the term of this patent is extended or adjusted under 35 U.S.C. 154(b) by 2309 days.

(21) Appl. No.: 12/372,300

(22) Filed: Feb. 17, 2009

(65) Prior Publication Data

US 2010/0211073 A1    Aug. 19, 2010

(51) Int. Cl.
*A61B 17/72* (2006.01)
*A61B 17/17* (2006.01)

(52) U.S. Cl.
CPC ...... *A61B 17/7225* (2013.01); *A61B 17/1739* (2013.01); *A61B 17/72* (2013.01); *A61B 17/1725* (2013.01); *A61B 17/7283* (2013.01)

(58) Field of Classification Search
CPC ....................................... A61B 17/72–17/7291
USPC ..................... 606/62–68, 246–279
See application file for complete search history.

(56) References Cited

U.S. PATENT DOCUMENTS

| | | | |
|---|---|---|---|
| 3,763,855 A | 10/1973 | McAtee | |
| 4,212,294 A | 7/1980 | Murphy | |
| 4,622,959 A | 11/1986 | Marcus | |
| 5,057,103 A | 10/1991 | Davis | |
| 5,084,053 A * | 1/1992 | Ender | 606/104 |
| 5,374,235 A * | 12/1994 | Ahrens | 606/101 |
| 5,549,609 A | 8/1996 | Frankel et al. | |
| 5,879,352 A * | 3/1999 | Filoso et al. | 606/62 |
| 6,077,264 A | 6/2000 | Chemello | |
| 6,224,600 B1 | 5/2001 | Protogirou | |
| 6,402,753 B1 | 6/2002 | Cole et al. | |
| 6,508,820 B2 | 1/2003 | Bales | |
| 6,579,293 B1 * | 6/2003 | Chandran | 606/64 |
| 7,090,676 B2 | 8/2006 | Huebner et al. | |
| 2001/0012939 A1 * | 8/2001 | Wahl et al. | 606/67 |
| 2003/0040747 A1 | 2/2003 | Dean | |
| 2005/0096656 A1 * | 5/2005 | Behrens | 606/64 |
| 2005/0177158 A1 * | 8/2005 | Doubler et al. | 606/64 |
| 2005/0278029 A1 * | 12/2005 | Trieu | 623/17.16 |
| 2006/0084998 A1 | 4/2006 | Levy | |
| 2006/0175785 A1 * | 8/2006 | Hamm | 280/124.106 |
| 2006/0200143 A1 | 9/2006 | Warburton | |
| 2007/0069493 A1 * | 3/2007 | Sanders | 280/89 |
| 2007/0260247 A1 * | 11/2007 | Semet | 606/62 |

OTHER PUBLICATIONS

Meyer et al, "A Biomechanical Comparison of an Intramedullary Nail and a Fixed Angle Screw Side Plate for Distal Femur Fractures", Orthopaedic Research Laboratories, 2007; 1-4.

* cited by examiner

*Primary Examiner* — Nicholas Plionis
(74) *Attorney, Agent, or Firm* — Occhiuti & Rohlicek LLP

(57) ABSTRACT

A device and method of stabilizing a fracture of a bone is provided. The device includes an intramedullary rod having a shaped distal end, and an insertion jig detachably connectable to the proximal end of the rod and used with the rod to apply a compressive force to the fracture site. The jig may also be used to correctly place fixation screws in a proximal end of the rod. The device achieves both fixation of the rod to the bone regardless of rod or bone diameter and allows for compression at the fracture site. In addition, fixation of the rod to the bone is accomplished without requiring a precise alignment of a distal end fixation screw. The device uses headless fixation screws, which, when in place, are disposed below cortical surface of bone, reducing damage to overlying soft tissues.

13 Claims, 12 Drawing Sheets

INTRAMEDULLARY COMPRESSION ROD

BACKGROUND OF THE INVENTION

Field of the Invention

This invention relates to devices and methods for fixation and compression of bone fractures.

Description of the Background Art

It is well known to use rigid internal fixation devices including rods, plates and wires to position and stabilize fractures of the long bones of the body to achieve successful bone healing. Known internal fixation devices are typically fixed to a bone using one or more screws. In some fractures of the long bones, a common approach for aligning the bone fragments is to insert a rod through the intradullary cavity. The rod may be held in place by screws until the fracture has healed, or may be left in the bone after healing is complete.

Conventional intramedullary rods, such as those used in the femur, often include an elongate rod that extends across the fracture and is fixed to the bone on each side of the fracture using screws that pass through holes provided in the rod. However, it is difficult to fix smaller diameter long bones such as the ulna of the forearm using this type of device because of the small bone diameter. In particular, the small rod diameter required for use in a small diameter long bone such as the ulna precludes providing through holes in the rod. As a result, it is difficult to fix the rod to the bone. Thus, a need exists for an intramedullar rod for use in small diameter long bones.

SUMMARY

A device and method of stabilizing a fracture of a bone is provided. The device may include an intramedullary rod. The distal end (furthest away from the body) of the rod is shaped to engage a distally placed screw, and a proximal end (nearest the body) of the rod may include through holes to receive fixation screws. The device may further include an insertion jig that detachably connects to the proximal end of the rod and may be used to apply a compressive force to the fracture site whereby displaced fractures may be closed. The jig may also be used to correctly place proximal end fixation screws in a proximal end of the rod. Among other advantages, the device provides an intramedullary rod that achieves fixation of the rod to the bone on opposed sides of the fracture regardless of rod or bone diameter, providing rotational control of the fracture, and also allows for compression at the fracture site. In addition, fixation of the rod to the bone is accomplished without requiring a precise alignment of a distal end fixation screw. Still further, the device uses headless fixation screws, which, when in place, are disposed below cortical surface of bone, reducing damage to overlying soft tissues.

In some approaches, an intermedullary device is provided for use in stabilizing a fracture of a bone. The device includes a rod having a longitudinal axis. A plurality of recesses are formed along an outer surface of the rod in a direction transverse to the axis. Each recess includes an engaging surface extending substantially transverse to the axis, and a sliding surface extending longitudinally from the engaging surface. The device further includes a rod engaging member having a first surface configured to engage a respective one of the plurality of sliding surfaces of the rod, and a second surface configured to engage a respective one of the plurality of engaging surfaces of the rod.

The intramedullary device may include one or more of the following features:

Each recess is elongate such that the dimension parallel to the longitudinal axis of the rod is greater than the dimension transverse to the longitudinal axis of the rod. Each recess further includes a curved surface opposed to the engaging surface, and the curved surface faces an insertion end of the rod. The rod engaging member is a headless screw. The rod includes a first end, a second end, and a midpoint between the first and second ends, and the recesses are disposed between the first end and the midpoint. The second end of the rod includes at least one through hole configured to receive an interlock screw. The interlock screw is configured to simultaneously engage bone on transversely opposed sides of the rod when received in a corresponding through hole. An end of the rod includes a first through hole configured to receive a first interlock screw and a second through hole configured to receive a second interlock screw. The first through hole extends transverse to the longitudinal axis, and the second through hole extends both transverse to the longitudinal axis and at an angle to the at least one first through hole. The intermedullary device further comprises a compression generating device configured to engage the proximal end of the rod and axially move the rod relative to the bone.

In some approaches, a rod insertion jig is provided for use with an intramedullary rod. The jig includes a threaded connector member including one end detachably connected to threads formed in an opening provided in an end of the rod. The jig includes a main body having a main body through hole in which is positioned a first mid-portion of the threaded connector member. The jig includes a receiving shaft disposed between the second end of the rod and the main body. The receiving shaft has a shaft first end which engages the second end of the rod, a shaft second end opposed to the shaft first end and having exterior threads, and a shaft axial through hole in which is positioned a second mid-portion of the threaded connector member. The jig includes a compression device coaxially disposed on the receiving shaft, the compression device including interior threads configured to engage the exterior threads of the receiving shaft. The jig further includes a securing nut disposed on the threaded connector member adjacent the main body and on a side of the main body opposed to receiving shaft, the securing nut serving to maintain the relative positions of the rod and receiving shaft with respect to the main body, and a buttress plate having a plate through hole that receives the shaft first end therethrough. In the rod insertion jig, a rotation of the compression device relative to the receiving shaft results in an axial movement of the buttress plate relative to the second end of the rod.

The jig may include one or more of the following features:

The buttress plate includes a first face which abuts an end of the compression device and a second face opposed to the first face, the buttress plate further including a plurality of axially-extending protrusions formed on the second face. The buttress plate freely axially slides relative to the receiving shaft. The main body includes a base portion including a first base arm and second base arm, and the base portion lies in a plane transverse to a longitudinal axis of the receiving shaft. In addition, a posterior arm extends orthogonally from an end of the first base arm toward the rod such that the posterior arm extends substantially parallel to the longitudinal axis, and a lateral arm extends orthogonally from an end of the second base arm toward the rod such that the lateral arm extends substantially parallel to the longitudinal axis. The posterior arm includes one or more posterior arm guide holes which extend through the posterior arm, and the lateral arm includes one or more lateral arm guide holes which extend through the lateral arm. The posterior and lateral guide holes are each respectively oriented to extend along an axis that intersects the longitudinal axis of the rod.

In some approaches, a bone compression device is provided for stabilizing a bone fracture. The device includes an intramedullary rod and rod insertion jig detachably connected to the rod. The intramedullary rod includes a first end configured to be fixed relative to the bone on a first side of the bone fracture, a second end configured to be fixed relative to the bone on a second side of the bone fracture, and a rod longitudinal axis. The rod insertion jig includes a threaded connector member including one end detachably connected to threads formed in an opening provided in the second end of the rod, and a main body including a main body through hole in which is positioned a first mid-portion of the threaded connector member. The jig includes a receiving shaft disposed between the second end of the rod and the main body, the receiving shaft having a shaft first end which engages the second end of the rod, a shaft second end opposed to the shaft first end and having exterior threads and a shaft axial through hole which in which is positioned a second mid-portion of the threaded connector member. The jig includes a compression device coaxially disposed on the receiving shaft, the compression device including interior threads configured to engage the exterior threads of the receiving shaft. The jig includes a securing nut disposed on the threaded connector member adjacent the main body and on a side of the main body opposed to receiving shaft, the securing nut serving to maintain the relative positions of the rod and receiving shaft with respect to the main body. The jig further includes a buttress plate having a plate through hole that receives the shaft first end therethrough. A rotation of the compression device relative to the receiving shaft results in an axial movement of the buttress plate relative to the second end of the rod.

The bone compression device may include one or more of the following features:

The buttress plate includes a first face which abuts an end of the compression device and a second face opposed to the first face, the buttress plate including a plurality of axially-extending protrusions formed on the second face. The buttress plate freely axially slides relative to the receiving shaft. The intramedullary rod further comprises a plurality of recesses formed along an outer surface of the rod in a direction transverse to the axis, each recess including an engaging surface extending substantially transverse to the axis, and a sliding surface extending longitudinally from the engaging surface. The intramedullary rod further includes a plurality of through holes formed adjacent the second end configured to receive second end fixation screws. The device further includes a first end fixation screw including a first surface configured to engage one of the sliding surfaces of the rod and a second surface configured to engage one of the engaging surfaces of the rod.

In some approaches, a method is provided for stabilizing a bone fracture using an intramedullary rod and rod insertion jig detachably connected to the rod. The rod includes a first end, a second end opposed to the first end, a longitudinal axis, a plurality of through holes formed at the second end, and a plurality of recesses formed along an outer surface of the first end in a direction transverse to the axis. Each recess includes an engaging surface extending substantially transverse to the axis, and a sliding surface extending longitudinally from the engaging surface. The jig includes a main body, a connector that detachably connects the main body to the second end of the rod, and a compression generating device configured to move the rod in an axial direction relative to the bone. The method includes the following method steps:

Inserting the rod in a medullary cavity of the bone so that the rod longitudinal axis is aligned with a longitudinal direction of the bone, and the first end of the rod and the second end of the rod reside on opposed sides of the fracture;

Inserting a first screw in the bone in a direction transverse to longitudinal axis and at a location between the first end of the rod and the fracture;

Actuating the compression generating device to axially move the rod whereby the engaging surface of one of the recesses engages a side surface of the first screw;

Further actuating the compression generating device to axially move the rod until the rod and bone are in a desired relative position;

Inserting one or more second screws in corresponding ones of the through holes so that the second screws reside within and extend outwardly from opposed sides through holes; and Detaching the rod insertion jig from the second end of the rod.

The method may include one or more of the following:

The step of inserting a first screw further includes inserting the first screw to the extent that an end of the first screw contacts the sliding surface of the rod, and the other end of the screw is engaged with cortical bone. After the step of further actuating the compression generating device, the method further includes advancing the first screw until a surface of the rod contacts an interior surface of the medullary cavity. After the rod insertion jig is detached from the second end of the rod, the second end of the rod resides at or below the cortex of the bone. After insertion, at least one of the first screw and one or more second screws is seated at or below the cortex of the bone. The step of further actuating the compression generating device is continued until a compression force is applied to the bone at the fracture. The first screw comprises a flat tip, and wherein when the flat tip is in contact with the sliding surface of the rod, rotation of the rod relative to the bone is prevented.

In some approaches, a bone compression device is provided for stabilizing a bone fracture. The device includes an intramedullary rod and rod insertion jig detachably connected to the rod. The device is configured to achieve and maintain compression of the fracture, and control rotation of the fracture.

The bone compression device may include one or more of the following features:

Control of rotation of the fracture comprises preventing rotation of a bone portion on one side of the fracture relative to a bone portion on an opposed side of the fracture. The intramedullary rod is configured to be fixed to the bone on opposed sides of the fracture whereby rotational control of the fracture is achieved. The fracture divides the bone into a first bone portion and a second bone portion, and the intramedullary rod is configured to engage with the first bone portion, and the rod insertion jig is configured to draw the first bone portion toward the second bone portion, whereby compression of the fracture is achieved.

Modes for carrying out the present invention are explained below by reference to an embodiment of the present invention shown in the attached drawings. The objects, characteristics and advantages of the present invention will become apparent form the detailed description of the embodiment of the invention presented below in conjunction with the attached drawings.

DETAILED DESCRIPTION

Figure 1:
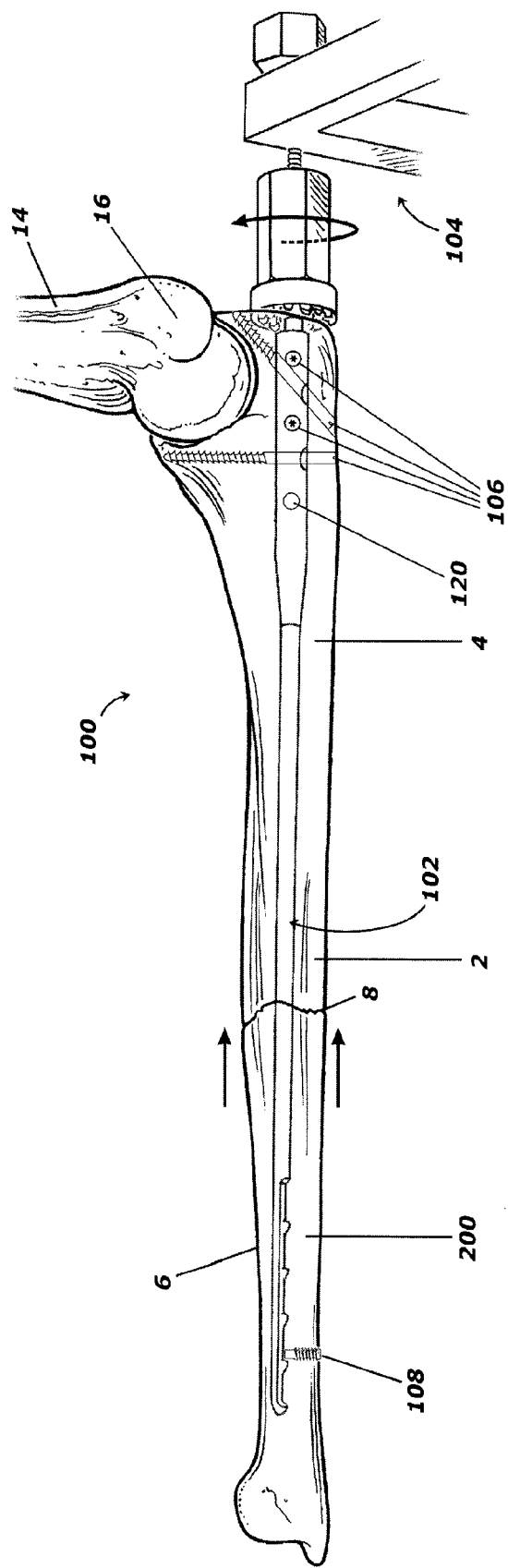
FIG. 1 is a side view of a bone compression device including an intramedullary rod disposed within the medullary cavity of an ulna and an insertion jig connected to a proximal end of the rod.
Figure 4:
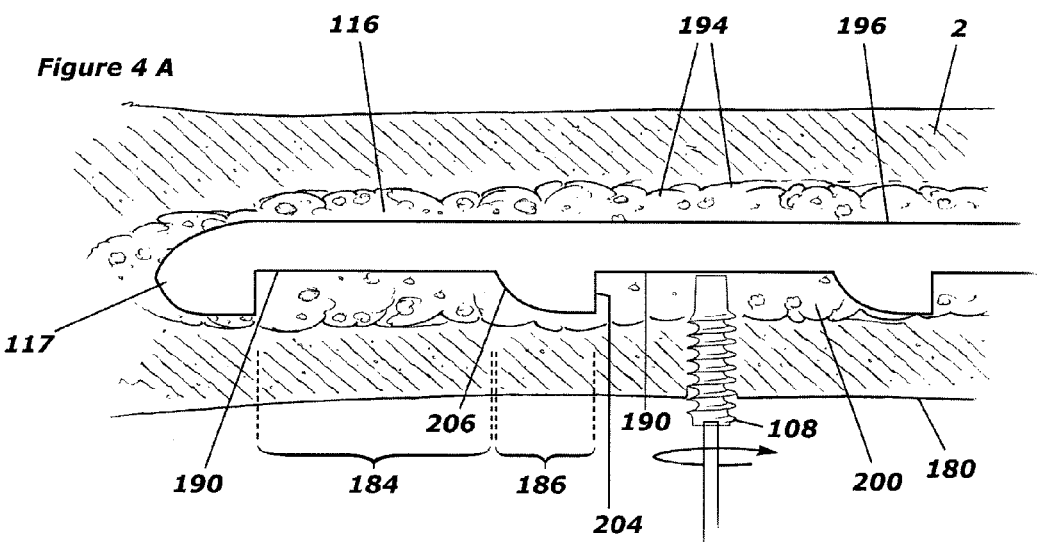
FIGS. 4a-4c are side sectional views of a distal end of the rod disposed within the medullary cavity.
Figure 4:
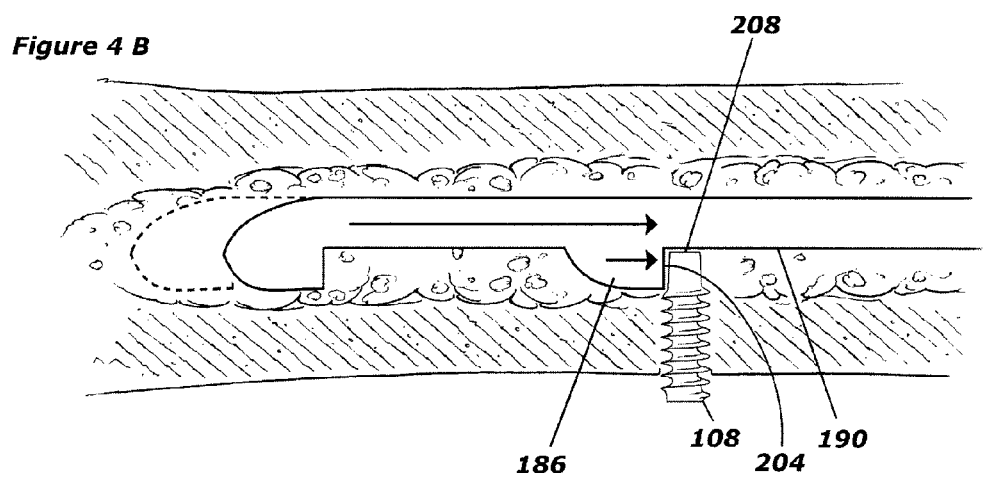
Figure 4:
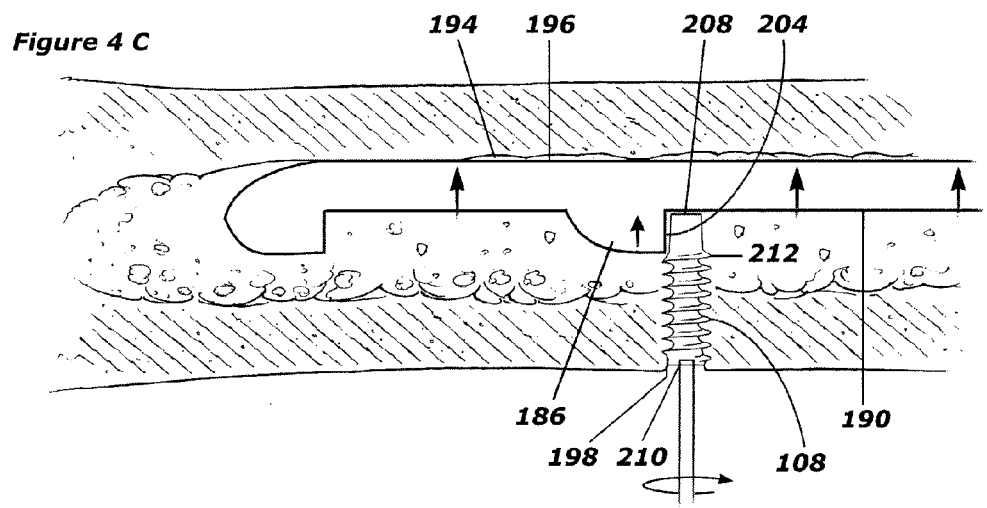

Referring to FIG. 1, an ulna 2 is shown connected to a humerus 14 via an elbow joint 16. A fracture 8 is shown in the mid-shaft of the ulna 2, dividing the ulna 2 into a proximal bone portion 4 and a distal bone portion 6. A compression device 100, including an intramedullary rod 102 and rod insertion jig 104, is shown with the rod 102 disposed within the medullary canal 200 (FIGS. 4, 13) of the ulna 2. The rod 102 is fixed relative to the distal bone portion 6 using a distal screw 108, and is fixed relative to the proximal bone portion 4 using one or more proximal interlock screws 106. When used in combination with the rod insertion jig 104, the rod 102 serves to compress the proximal and distal bone portions 4, 6 of the ulna 2 together. Once the proximal and distal bone portions 4, 6 are properly mutually positioned, the rod insertion jig 104 may be disconnected from the rod 102, and the rod 102 remains within the medullary canal 200 of the ulna 2 to provide compression and fixation of the proximal and distal bone portions 4, 6.

Figure 2:
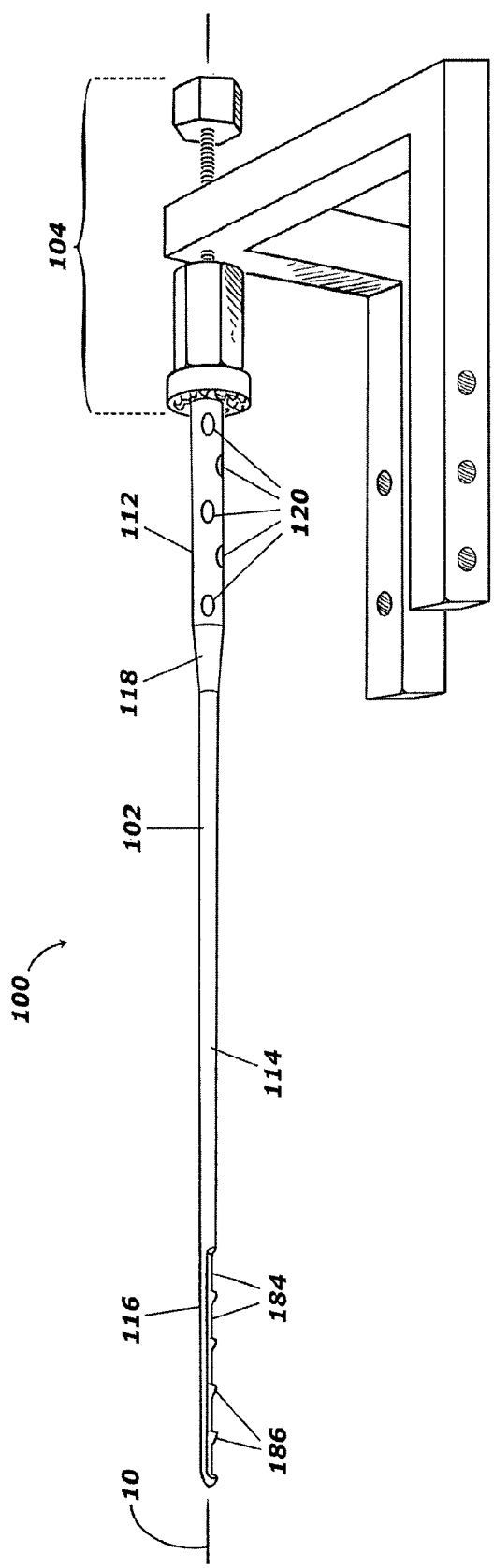
FIG. 2 is a perspective view of the bone compression device of FIG. 1.

Referring to FIG. 2, the compression device 100 is shown isolated from the ulna 2. As seen in this figure, the rod 102 is an elongate, solid member including a generally cylindrically shaped proximal end 112 that is configured to connect to the rod insertion jig 104. The rod 102 includes a distal end 116 opposed to the proximal end 112. An elongate cylindrical mid-portion 114 extends along a longitudinal axis 10 between the proximal and distal ends 112, 116, and has a cross-sectional diameter that is less than that of the proximal end 112. In some embodiments the cross sectional diameter of the mid portion 114 is about half that of the proximal end 112.

The proximal end 112 of the rod 102 has a tapered portion 118 to provide a smooth transition between the proximal end 112 and the mid-portion 114, a feature which reduces injury to the interior surface of the medullary canal 200 during insertion of the rod 102 in the ulna 2. The proximal end 112 includes one or more through holes 120 that receive the proximal interlock screws 106 to maintain proximal and distal positioning of the rod 102 and prevent rotation of the rod 102 with respect to the proximal bone portion 4. In the illustrated embodiment, five through holes 120 are provided. In some embodiments, a first subset of through holes 120 are aligned transverse to the longitudinal axis 10 of the rod 102, and a second subset of through holes 120 are aligned at an acute angle with respect to both the longitudinal and transverse axes of rod 102. At least one proximal interlock screw 106 is required to achieve sufficient fixation of the proximal end 112 of the rod 102 with respect to the proximal end 4 of the ulna 2, and a more secure fixation is achieved if more than one proximal interlock screws are used.

Figure 3:
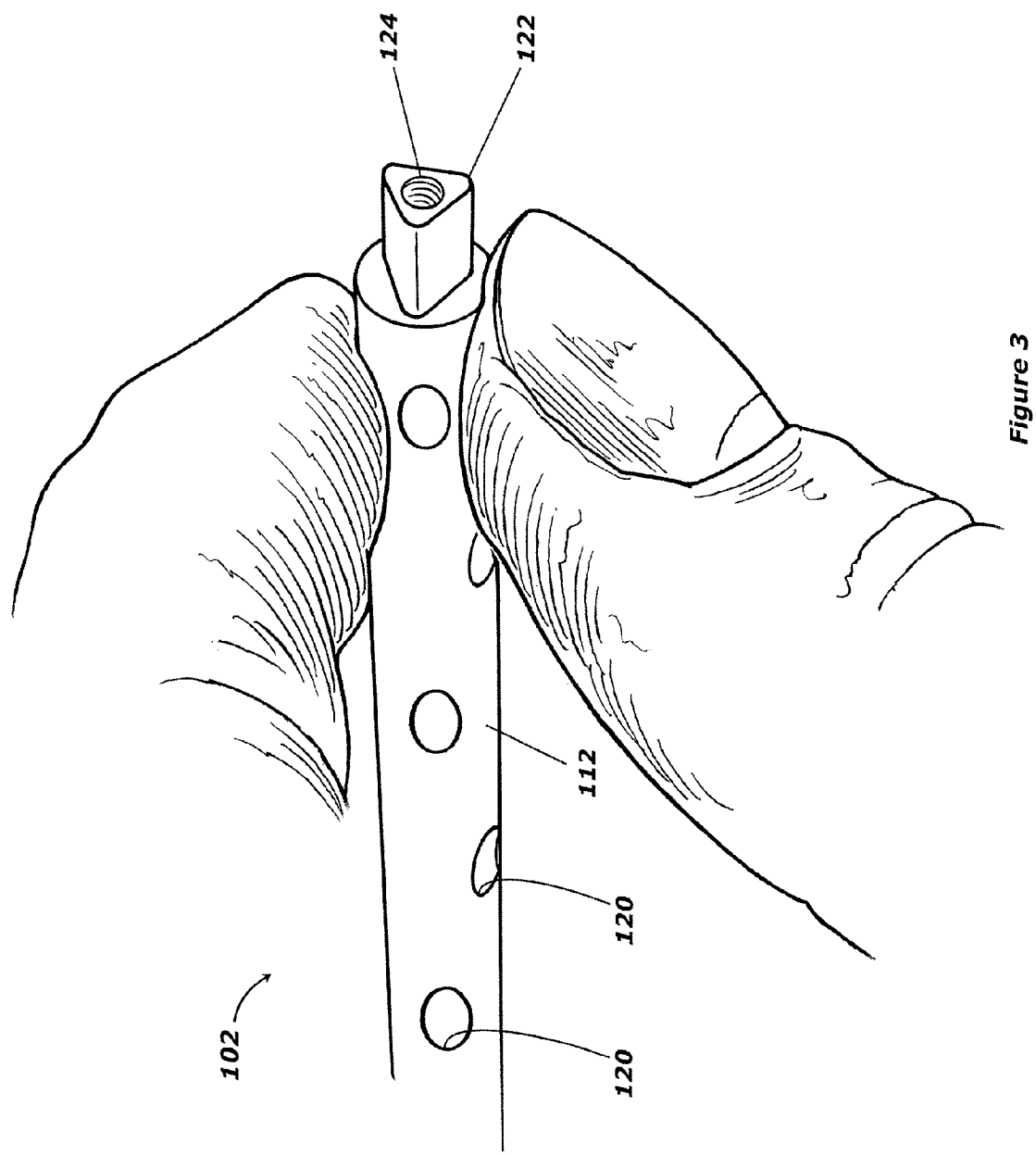
FIG. 3 is a perspective view of the proximal end of the rod of FIG. 1.

Referring to FIG. 3, the most proximal portion of the rod 102 includes a triangular shaped jig interface 122. The triangular interface 122 is received in a complimentarily shaped opening in the alignment jig 104, and serves to prevent rotation of the rod 102 with respect to the rod insertion jig 104 when connected thereto. The interface is not limited to a triangular shape, and other noncircular (e.g. square, oval, etc.) interfaces or interlocking tabs could be used to prevent the rod 102 from rotating relative to the rod insertion jig 104. A threaded receiving hole 124 is drilled longitudinally in the center of the triangular shaped jig interface 122. The receiving hole is sized to receive a correspondingly threaded connector 134 (described below) when the rod 102 is connected to the insertion jig 104.

Referring to FIG. 4a, an enlarged view of the distal end 116 of the rod 102 is shown positioned within the medullary canal 200 of the ulna 2. The distal tip 117 of the rod 102 is rounded to allow it to pass easily through the medullary canal 200. The distal end 116 of the rod 102 includes several recesses 184 formed along an outer surface of the rod 102 in a direction transverse to the axis 10. Each recess 184 is elongate in the axial direction of the rod 102. That is, the recess dimension parallel to the longitudinal axis 10 is greater than the recess dimension transverse to the longitudinal axis 10. Each 184 recess includes a flat face 204 which faces toward the proximal end 112 of the rod 102 and which provides an engaging surface for a rod-engaging distal screw 108 (discussed below) placed in the posterior cortex 180 of the ulna 2. The flat face 204 extends substantially transverse to the axis 10. Each recess 184 also includes a flat portion 190 which serves as a sliding surface for the distal screw 108. The flat portion 190 extends longitudinally from the engaging surface 204. Each recess 184 further includes a curved surface 206 opposed to the engaging surface 204. The curved surface 206 faces an insertion (distal) end of the rod 102. The curved shape of the surface 206 eases insertion of the rod 102 and helps to minimize injury to the interior bone surfaces during insertion.

The recesses 184 are separated by portions of the rod referred to as protrusions 186. The protrusions 186 are approximately ½ to ⅓ the diameter of the mid portion 114 of the rod in height. They extend outwardly from the flat portion 190 and therefore the overall diameter of the distal end of the rod 116 including the protrusions 186 is no greater in diameter than the mid portion 114 of the rod. Each protrusion 186 is defined by the flat face 204 of one recess 184, and the curved face 206 of the adjacent recess 184. In some embodiments, the protrusions 186 are spaced at regular intervals. The interval spacing may be, for example, approximately 1.5 cm, but is not limited to this spacing. The protrusions 186, particularly the flat faces 204 thereof, are used to engage the distal screw 108.

Compression of the Displaced Fracture

Initially, or prior to compression of the displaced fracture 160 (described below), the distal screw 108 is directed transverse to the axis of the rod 102 and set proximally to distally between protrusions 186 on the distal end of the rod 116. The distal screw 108 is advanced until it just touches but does not exert pressure against the flat portion 190 of the rod 102 (FIG. 4A). During the initial placement of the distal screw 108, prior to compression of the displaced fracture 160 (described below), the posterior aspect of the rod 196 is not firmly pressed up against the far endosteal surface 194 of the ulna 2.

Compression of the displaced fracture 160 is achieved by retracting the rod 102 proximally through actuation of compression nut 127 on the rod insertion jig 104 (discussed below). As the rod 102 is retracted proximally (the retraction direction is indicated by the long arrow in FIG. 4B), the distal screw 108 slides along the flat portion 190 until it engages the flat face 204 of a protrusion 186. At this point, a proximally directed force (indicated by the short arrow in FIG. 4B) is transmitted from the protrusion 186 of the rod 102 to the distal end of ulna 6 through the distal screw 108, providing compression of the displaced fracture 160. The tip 208 of the distal screw 108 is flat so that as it abuts the flat portion 190 of the rod 102, it provides rotational control of the distal portion 6 of the ulna 2 and the distal end 116 of the rod 102, preventing rotation of the distal portion 6 of the ulna 2 relative and the distal end 116 of the rod 102.

After the displaced fracture has been sufficiently compressed, the distal screw 108 is seated firmly against the flat face 204 of the protrusion 186. The distal screw 108 is then advanced until it pushes the posterior aspect of the rod 196 against the far endosteal surface of the bone 194 (FIG. 4C). The distal screw 108 is configured without a head so that the base 210 of the distal screw 108 is no greater in diameter than the main body 212 of the distal screw 108. In addition, the length of the distal screw 108 is such that, once in position, the base 210 is seated at or below the edge of the ulnar cortex 198. These features are advantageous since they minimize hardware irritation to overlying soft tissue. Additional distal screws 108 can be inserted to provide additional strength to the construct as needed.

Figure 5:
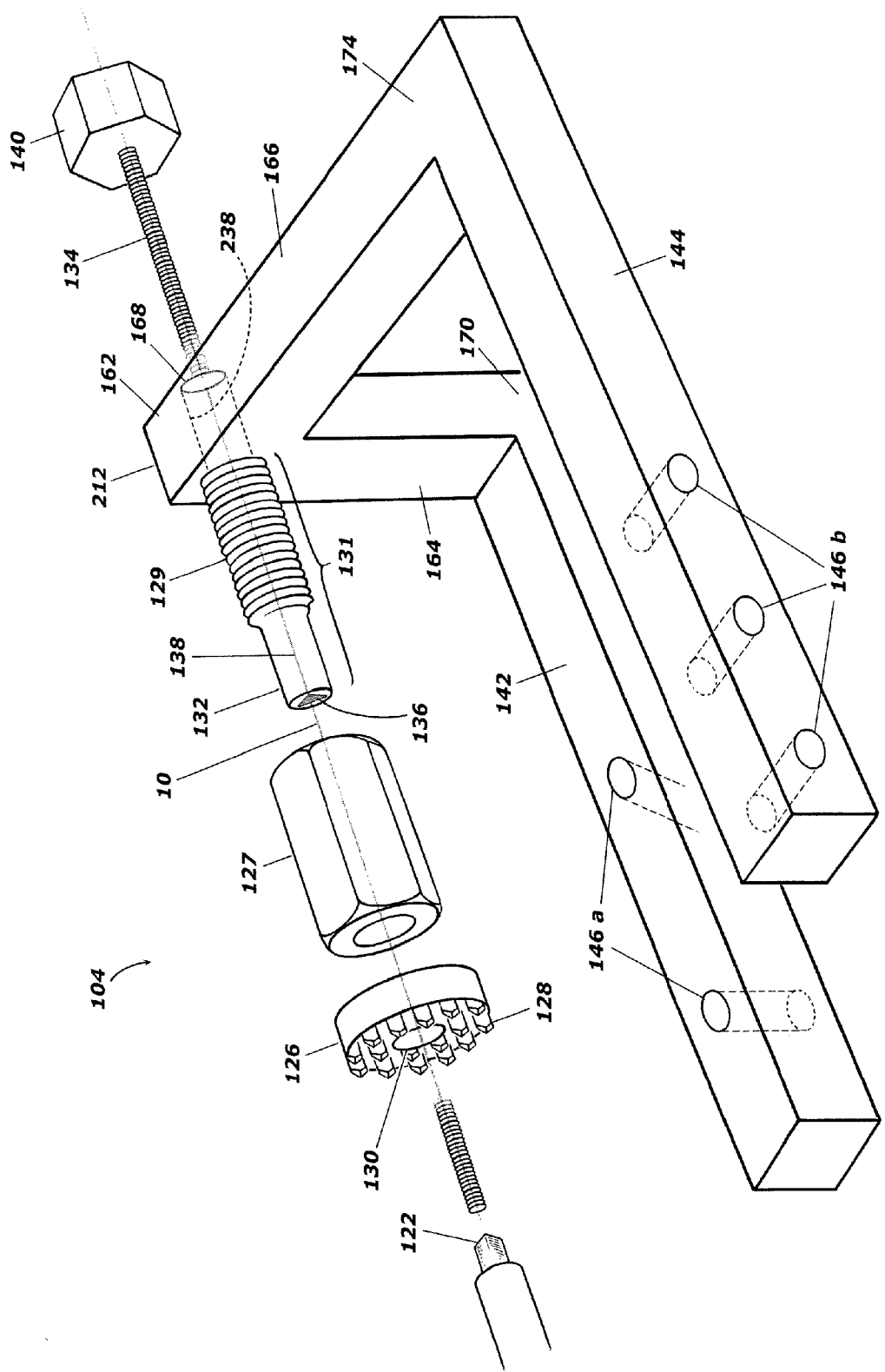
FIG. 5a is an exploded perspective view of the insertion jig of FIG. 1.
FIG. 5b is a side sectional view of the insertion jig connected to the rod.
Figure 5:
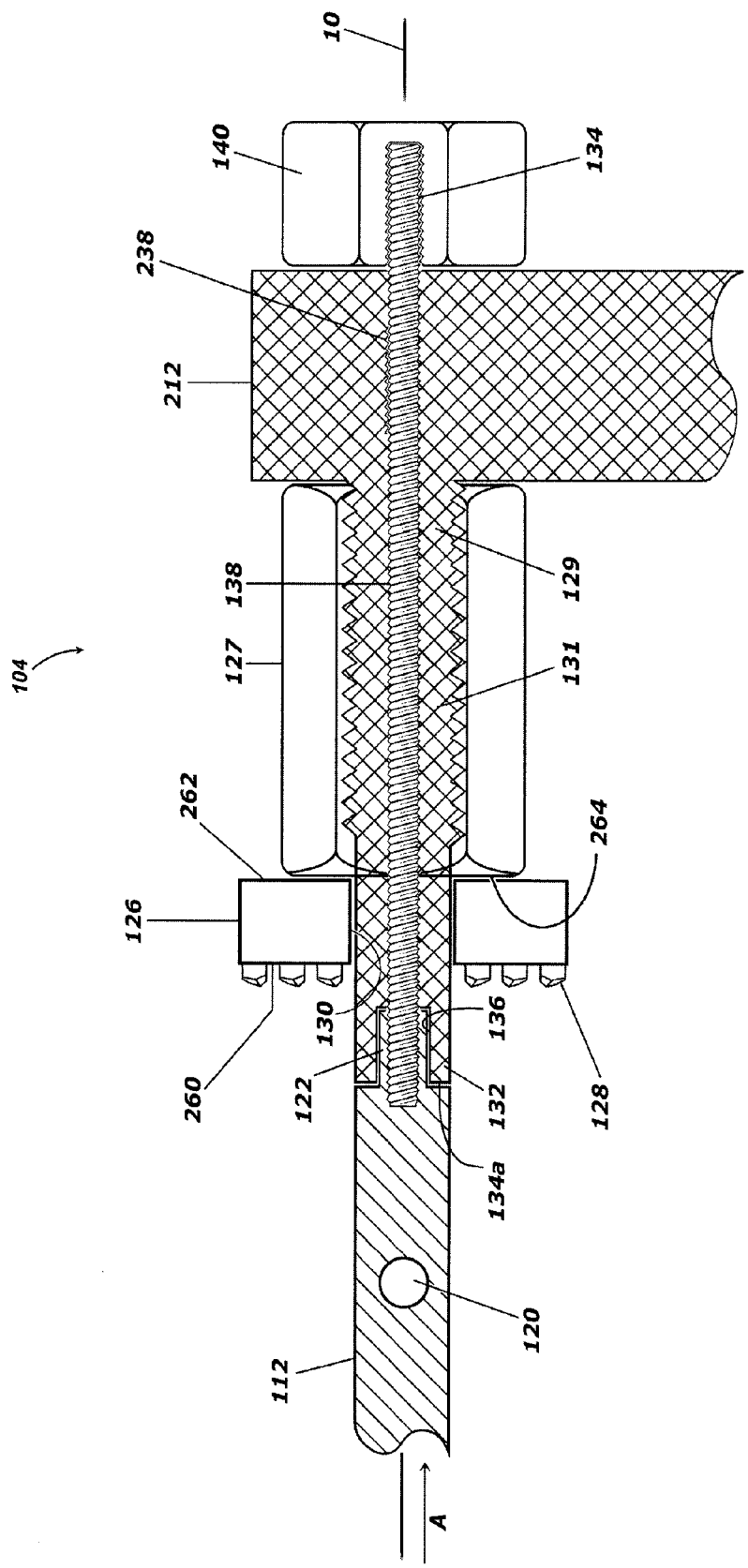

Referring to FIG. 5a (an exploded view) and FIG. 5b (a side section view), the insertion jig 104 includes a jig main body 212, a receiving shaft 131, a compression nut 127, a securing nut 140, a buttress plate 126, and a threaded connector member 134.

Figure 6:
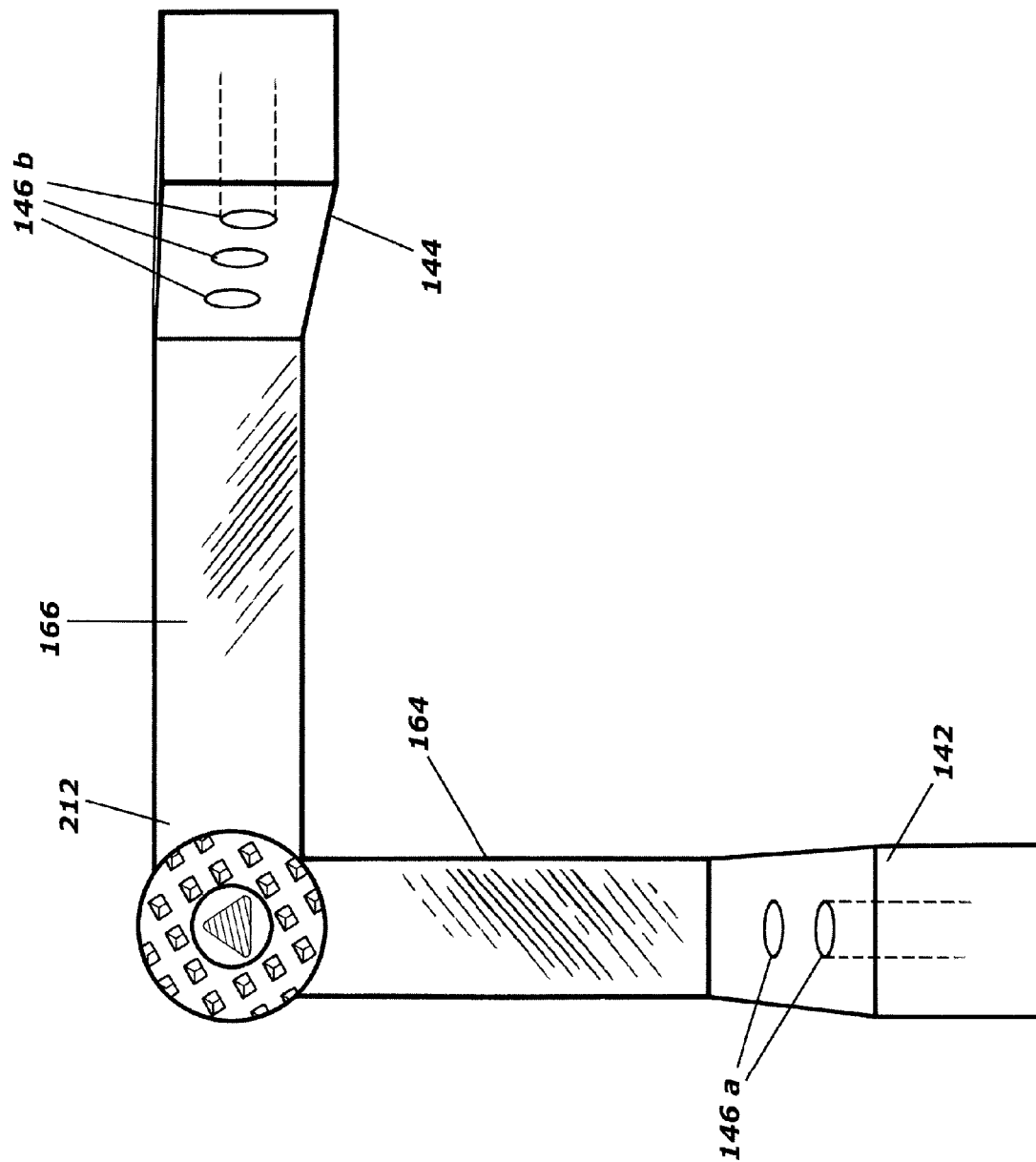
FIG. 6 is an end view of the insertion jig as seen in the direction of arrow A as shown in FIG. 5b.

The jig main body 212 is a rigid structure on which the remaining components of the insertion jig 104 are mounted. The main body 212 includes an L-shaped base portion 162 including a first base arm 164, and second base arm 166 that intersects the first base arm 164 at a right angle (FIG. 6). The base portion 162 is arranged to lie in a plane transverse to a longitudinal axis of the receiving shaft 131 (described below), which in turn is coaxial with the longitudinal axis 10 of the rod 102. The main body 212 includes a through hole 238 disposed substantially at the intersection of the first and second base arms 164, 166. The through hole 238 extends in parallel to the longitudinal axis 10 and is dimensioned to receive the threaded connector member 134 therethrough.

The jig main body 212 also includes a posterior arm 142 and a lateral arm 144 which extend in parallel to each other and the longitudinal axis 10 of rod 102. FIG. 6 illustrates the orthogonal orientation of the posterior arm 142 relative to the lateral arm 144 of the rod insertion jig 104. In addition, the posterior arm 142 extends orthogonally from an end 170 of the first base arm 164 toward the rod 102 such that the posterior arm 142 extends substantially parallel to the rod longitudinal axis 10. Similarly, the lateral arm 144 extends orthogonally from an end 174 of the second base arm 166 toward the rod 102 such that the lateral arm 144 extends substantially parallel to the rod longitudinal axis 10.

The posterior arm 142 includes one or more posterior arm guide holes 146a which extend through the posterior arm 142, and the lateral arm 144 includes one or more lateral arm guide holes 146b which extend through the lateral arm 144. The posterior and lateral guide holes 146a, 146b are each respectively oriented to extend along an axis that intersects the rod longitudinal axis 10, and are dimensioned to accommodate an outer diameter of proximal interlock screws 106 used to fix the rod 102 with respect to the proximal portion of the ulna 2. More specifically, when the alignment jig 104 is connected to the rod 102, the each of the guide holes 146a, 146b are arranged to be aligned with a corresponding hole 120 formed in the proximal end 112 of the rod 102. The guide holes 146a, 146b are dimensioned and arranged to facilitate both properly locating a drill site and subsequent drilling of the proximal end of the ulna 2, as well as placement of the proximal interlock screws 106 into the proximal end of the rod 112 (described below) once a corresponding bone hole has been drilled.

The receiving shaft 131 is disposed between the proximal end 112 of the rod 102 and the jig main body 212, and abuts one side of the base portion 162. The receiving shaft 131 includes a shaft first end 132 which engages the proximal end 112 of the rod 102, a shaft second end 129 opposed to the shaft first end 132 and having exterior threads, and a shaft axial through hole 138. The shaft axial through hole 138 is dimensioned to receive the threaded connector member 134 therethrough, and is continuous with the through hole 238 of the main body 212.

The shaft first end 132 has a smooth exterior surface and an outer diameter that is substantially the same as that of the rod 102. In addition, the shaft first end 132 has a triangular opening 136 sized to received the triangular shaped jig interface 122 provided on the proximal portion 112 of the rod 102. The jig interface 122 mates with the triangular hole 136 formed in the end face 132a of the shaft first end 132 to provide a secure connection and prevent relative rotational motion between the rod 102 and the receiving shaft 131. The exterior threads of the shaft second end 129 cooperatively engage threads formed on an inner surface of a compression nut 127 which is co-axially disposed on the proximal threaded end 129.

The compression nut 127 is long relative to its cross-sectional diameter. In some embodiments, the compression nut 127 has a hexagonal cross-sectional shape to permit the nut 127 to be easily manually grasped and rotated. In other embodiments, the compression nut has other polygonal cross-sectional shapes such as square or pentagonal.

The buttress plate 126 is a generally disc-shaped body that is larger in diameter than the proximal end of the rod 112.

The buttress plate 126 includes a first, proximally-directed face 262 which abuts an end 264 of the compression nut 127, and a second, distally-directed face 260 opposed to the first face 262. Sharp protrusions 128 are formed on the distally-directed face 260 of the buttress plate 126 and extend longitudinally toward the proximal end 112 of the rod 102. In some embodiments, the buttress plate 126 is approximately 5 mm greater in diameter than the proximal end of the rod 112. This size allows the buttress plate 126 to be small enough to pass inside the skin incision and large enough to distribute compressive forces against the proximal end of the ulna 2 and associated soft tissues. However, the diameter of the buttress plate 126 is not limited to this size.

The buttress plate 126 is disposed on the distal end 132 of the receiving shaft so that an end 264 of the compression nut 127 abuts the proximally-directed face 262 of the buttress plate 126. There exists a center hole 130 in the buttress plate 126, which is sized to permit the buttress plate 126 to slide freely over top of both the proximal end 112 of the rod 102 and/or over the smooth distal end 132 of the receiving shaft 131. Since the smooth distal end 132 of the receiving shaft 131 has the same diameter as the proximal end 112 of the rod 102, the proximal end 112 of the rod 102, as well as a portion of the smooth distal end 132 of the insertion jig 104 can be passed completely into the medullary canal 200 of the ulna 2. As a result, when the rod insertion jig 104 is removed, the triangular shaped jig interface 122 does not protrude proximally outside the edge of the bone 2.

The threaded connector member 134 is an elongate, rigid threaded rod used to interconnect the components of the insertion jig 104 and to connect the insertion jig 104 to the rod 102. In particular, when the rod 102 is assembled with the insertion jig 104, a first end of the threaded connector member 134 is received within the threaded receiving hole 124 of the proximal end 112 of the rod 102. The threaded connector member 134 extends serially through the buttress plate 126, compression nut 127 and main body 212 so that a mid portion of the threaded connector member 134 passes through axially aligned hole 138 formed in the receiving shaft 131 and axially aligned hole 238 formed in the main body 212 of the insertion jig 104. When the securing nut 140 on the proximal end of the threaded connector member 134 is tightened, the rod insertion jig 104 is firmly fixed to the rod 102 and the assembled configuration of the insertion jig 104 and the rod 102 is maintained.

Figure 7:
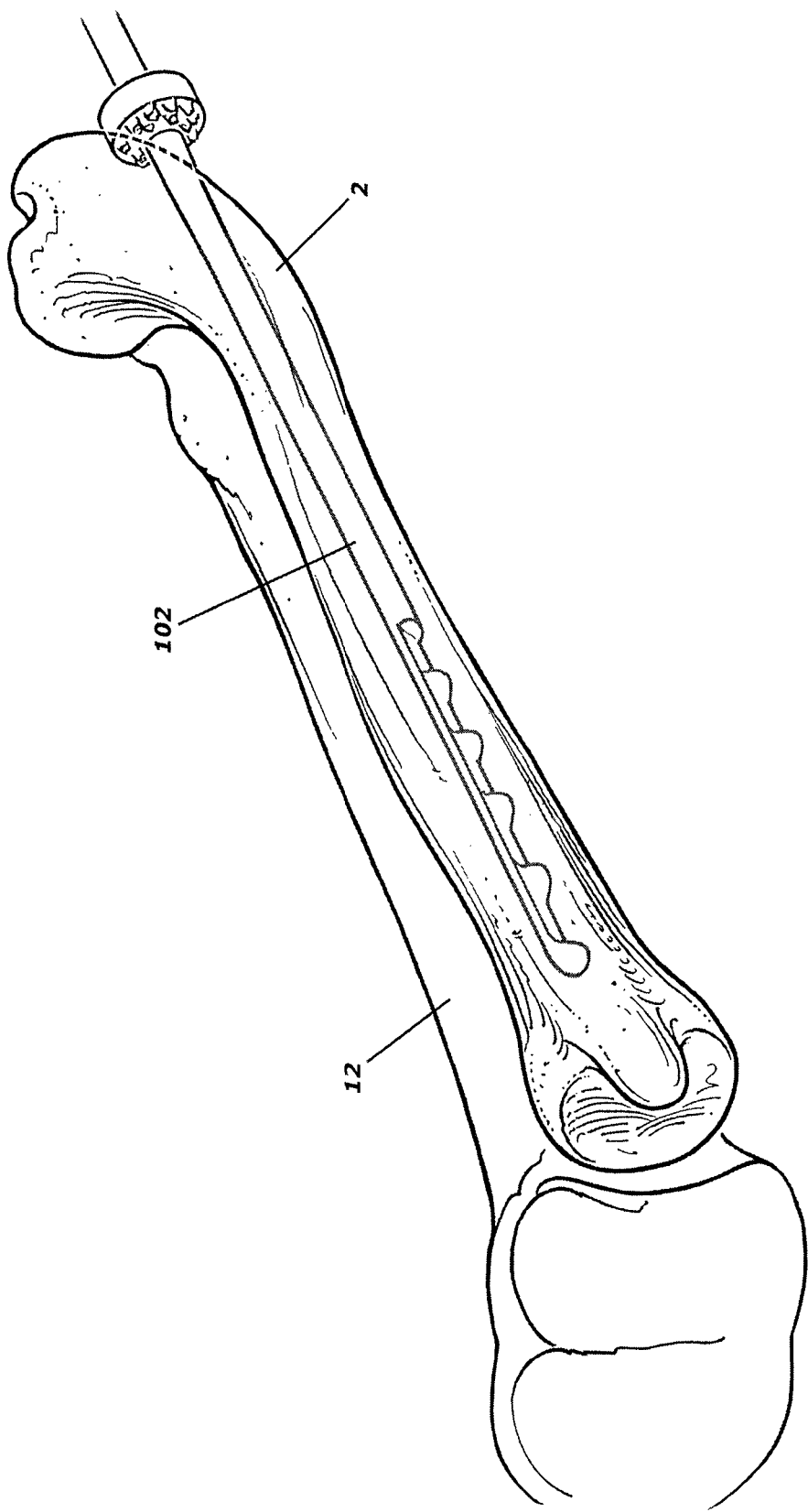
FIG. 7 is a perspective view of the forearm bones illustrating the rod disposed in the ulna and the radius shown lying in its normal position next to the ulna.

FIG. 7 demonstrates a foreshortened view of the rod 102 as it is placed in the ulna bone 2. The radius bone 12 is shown lying in its normal position next to the ulna bone 2.

A method of using the rod 102 and insertion jig 104 will now be described with reference to FIGS. 8-12.

Figure 8:
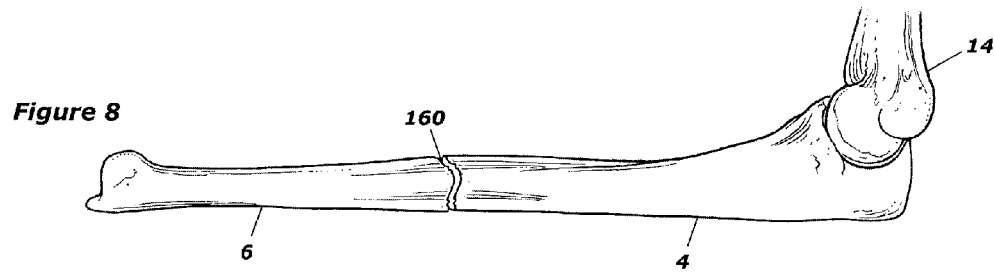
FIG. 8 is a side view of an ulna including a mid shaft displaced fracture.

FIG. 8 shows the ulna 2 with a displaced fracture 160, whose ends are not perfectly coapted, dividing the ulna into proximal bone portion 4 and distal bone portion 6. The humerus 14 helps clarify the proximal bone portion 4 of the ulna 2.

Prior to insertion of the rod 102, a first hole is drilled in the proximal cortex of the ulna 2 in a direction aligned with the longitudinal axis of the ulna to provide access to the intramedullary cavity 200. The first hole has a diameter just large enough to accommodate the outer diameter of the insertion rod 102.

Figure 9:
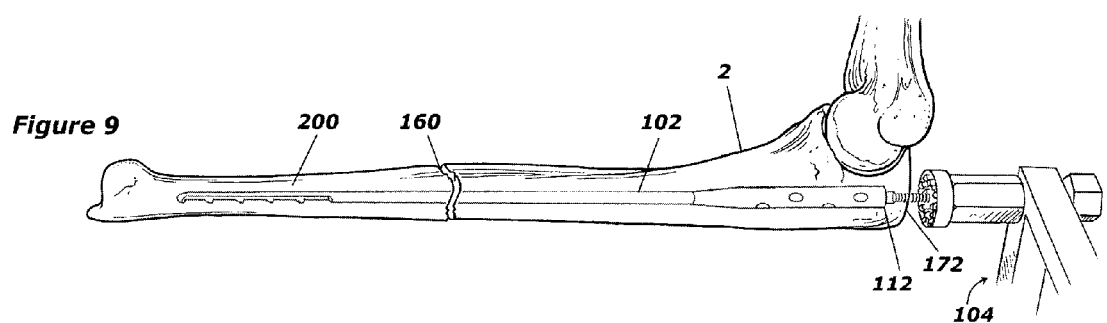
FIG. 9 is a side view of the ulna of FIG. 8 with the rod inserted in the medullary canal of the ulna.

The insertion rod 102, pre-assembled to compression jig 104, is inserted into the intermedullary cavity 200 so that the rod 102 extends axially within the cavity 200 and so that the proximal end 112 of the rod 102 and the distal end 112 of the rod 102 reside on opposed sides of the displaced fracture 160. FIG. 9 shows the ulna 2 with the rod 102 inserted. The proximal end of the rod 112 is seated so that it passes deep/distal to the proximal cortex 172 of the ulna 2.

Figure 10:
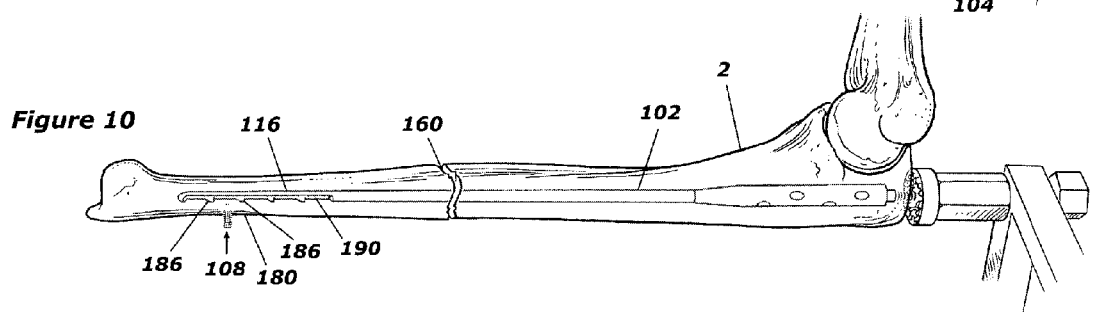
FIG. 10 is a side view of the ulna of FIG. 9 with a distal screw provided in the ulna at a location corresponding to a distal end of the rod.

Once the proximal end of the rod 112 is properly seated, a second hole is drilled in the posterior cortex 180 of the ulna 2 at a location distal to the displaced fracture 160 and which is aligned radiographically to be between any two protrusions 186. The second hole is drilled transverse to the longitudinal direction of the rod. FIG. 10 shows a distal screw 108 placed in the posterior cortex 180 of the ulna directed transverse to the axis of the rod 102 and set proximally to distally between protrusions 186 on the distal end of the rod 116. The distal screw 108 is advanced until it just touches but does not exert pressure against the flat part 190 of the rod 102. Advancement of the distal screw 108 may be done both by feeling for resistance against advancement by the surgeon and also by intraoperative x-ray.

Figure 11:
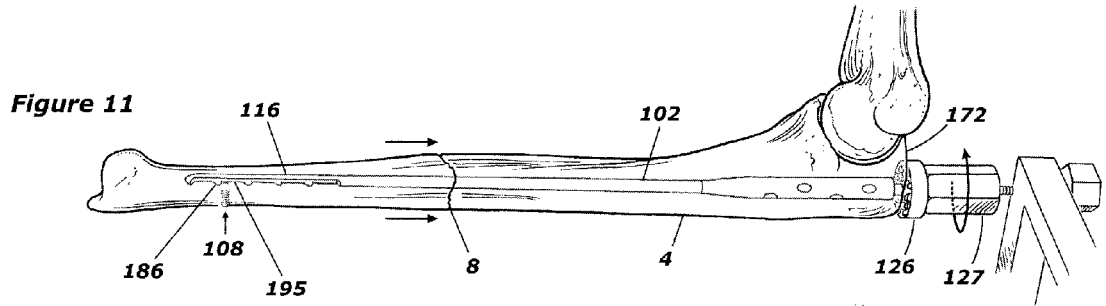
FIG. 11 is a side view of the ulna of FIG. 10 with the distal screw engaged with the distal end of the rod and the fracture reduced.

With the distal screw 108 in place with respect to the distal end 116 of the rod 102, the compression nut 127 is turned to retract the rod 102 (that is, move the rod 102 in a proximal direction) relative to the ulna 2 (FIG. 11). As the compression nut 127 is tightened, the buttress plate is pushed 126 against the proximal cortex of the ulna 172 as the distal end 116 of the rod 102 is pulled proximally. Once the protrusions 186 on the distal end 116 of the rod 102 engage the distal screw 108, the distal bone portion 6 is then pulled proximally to compress against the proximal bone portion 4. The displaced fracture 160 is now a reduced and compressed fracture 8. Adequate compression may be assessed by intraoperative x-ray.

Figure 12:
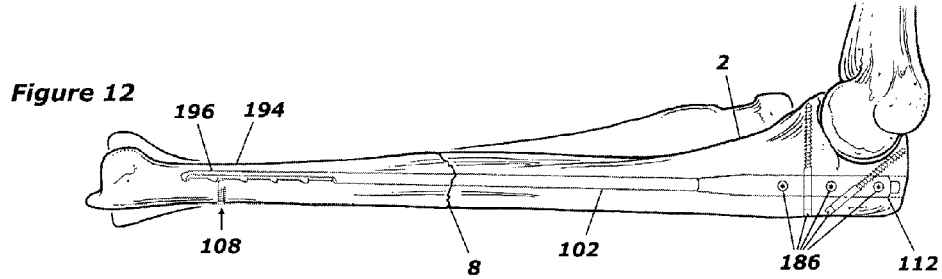
FIG. 12 is a side view of the ulna of FIG. 11 with proximal screws fixing the proximal end of the rod relative to the ulna.

Once the desired compression is achieved, the distal screw 108 is further advanced to seat the posterior aspect of the rod 196 against the far endosteal surface of the bone 194 as described above. At this time, additional holes are drilled in the proximal portion 4 of the ulna 2 by using the guide holes 146a, 146b provided in the main body 212 of the insertion jig 104. As discussed above, the guide holes 146a, 146b assure that the drilled holes are correctly aligned with the holes 120 in the proximal end 112 of the rod 102. After the holes are drilled, the guide holes 146 are used place proximal interlock screws 106 into the proximal end of the rod 112 (FIG. 12). The proximal interlock screws 106 are long relative to the diameter of the proximal end 112 of the rod 102 so that when in place, the opposed ends of the proximal interlock screws extend outwardly from opposed sides of the rod 102. In particular, the proximal interlock screws have a length on the order of that of the diameter of the proximal end of the ulna to maximize engagement with available cortical bone in this region, thus maximizing fixation of the proximal end 112 of the rod 102.

The proximal interlock screws 106 are placed to prevent rotation of the proximal portion 4 of the ulna 2 relative to the rod 102. Since the distal portion 6 of the ulna 2 was earlier fixed relative to the rod 102 via the distal screw 108, the ulna 2 is fixed to the rod 102 on opposed sides of the fracture, and thus the distal portion 6 and proximal portion 4 of the ulna 2 are prevented from relative rotation. In addition, this configuration maintains compression of the ulna 2 and fracture 8.

With the rod 102 fixed proximally and distally of the fracture 108, the rod insertion jig 104 is removed from the proximal end 112 of the rod 102, and the rod 102 remains in place within the intramedullary canal.

Figure 13:
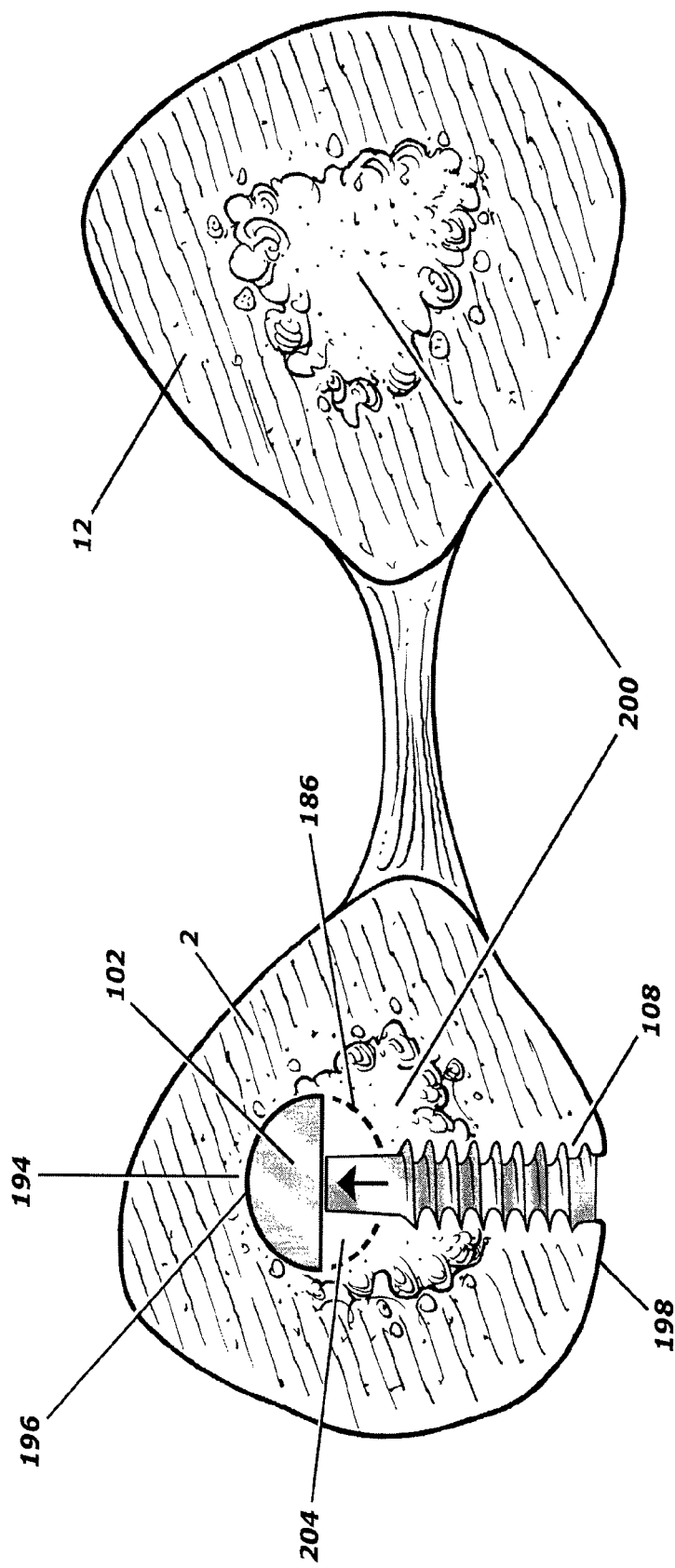
FIG. 13 is a sectional view of the distal end of the bones of the forearm with the rod inserted in the medullary canal of the ulna and distal screw in place.

FIG. 13 shows a cross sectional view of the distal end of the forearm as seen looking toward the hand, illustrating from a different view the position of the rod 102 within the intramedullary canal 200 after the distal screw 108 has been tightened. The protrusion 186 seats firmly against the distal screw 108 and the distal screw 108 pushes the posterior aspect of the rod 196 against the far endosteal surface of the bone 194. Once in position, the distal screw 108 is seated below the edge of the ulnar cortex 198 to minimize hardware irritation to overlying soft tissue.

Figure 14:
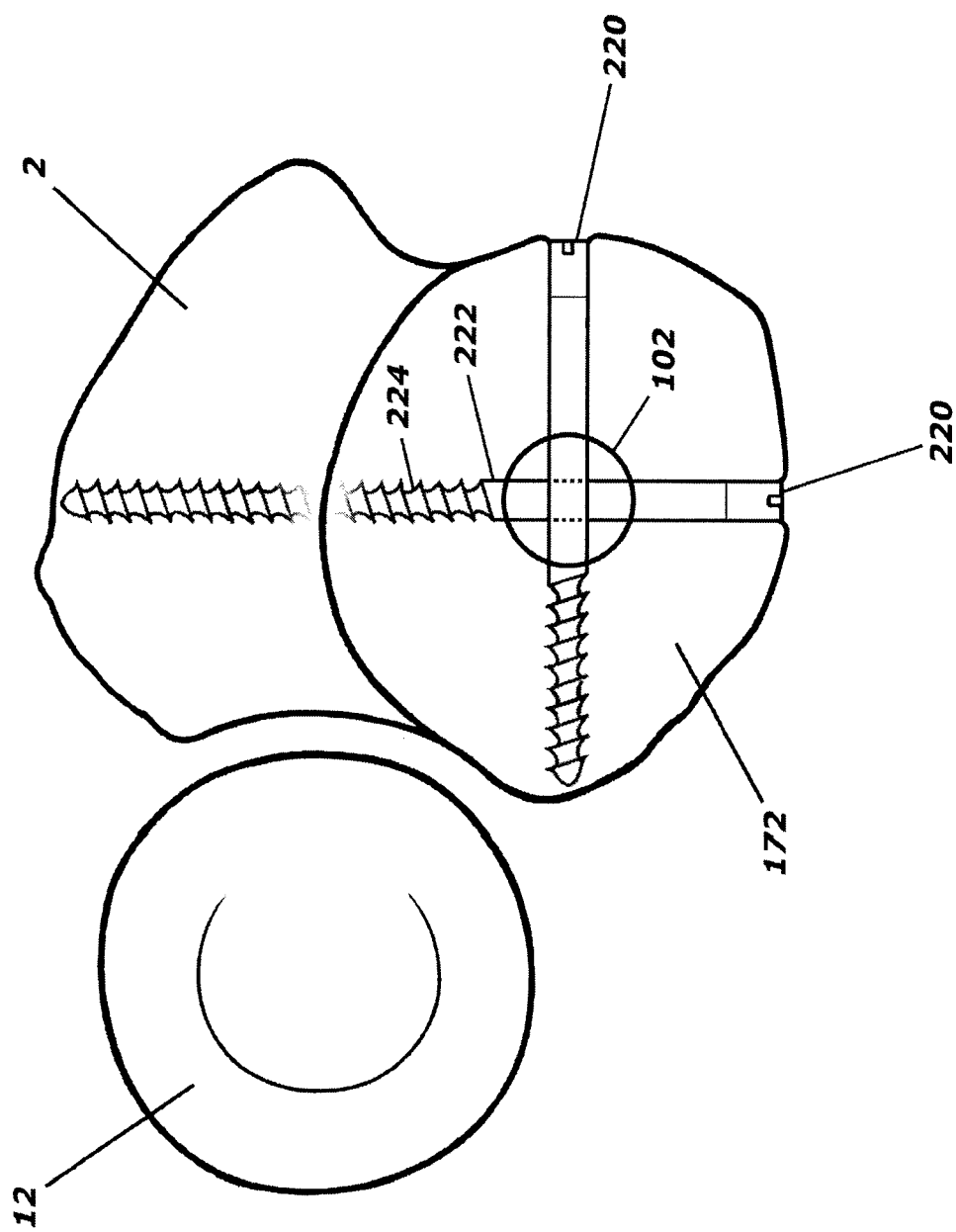
FIG. 14 is a sectional view of the proximal end of the ulna.

FIG. 14 is a cross sectional view of the proximal end of the forearm as seen looking toward the elbow, illustrating placement of the rod 102 along with the proximal interlock screws 106. This shows the orthogonal orientation of proximal screw 106 placement which provides secure fixation and can be beneficial when fracture lines propagate proximally. It also demonstrates that the proximal screws 106 are also headless constructs allowing them to be buried at or below the level of the cortex 220 to minimize soft tissue irritation. The proximal interlock screws 106 have a shaft 222 that is the same diameter as the outer part of the thread 224 of the screw. This provides for a secure fit between the interlock screw shaft 222 and the holes 120 in the rod 102.

Figure 15:
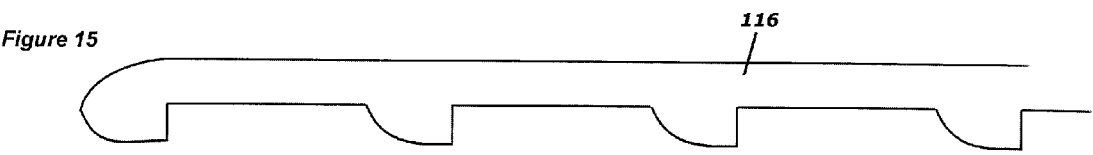
FIG. 15 is a schematic side view of the distal end of the rod of FIG. 1 to use as comparison for FIG. 16A-D.

FIG. 15 is a schematic side view of the distal end 116 of the rod 102 which can be used for a basis of comparison to other configurations of the distal end of the rod demonstrated in FIGS. 16A-D, which would achieve the same ability to lock the distal end and provide compression, but are of slightly different shape.

Figure 16:
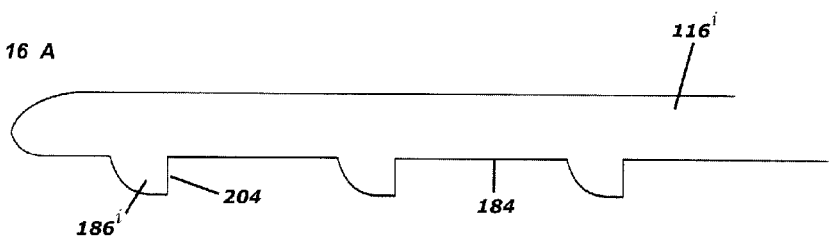
FIG. 16A-D are schematic side views of alternative embodiments of the distal end of the rod.
Figure 16:
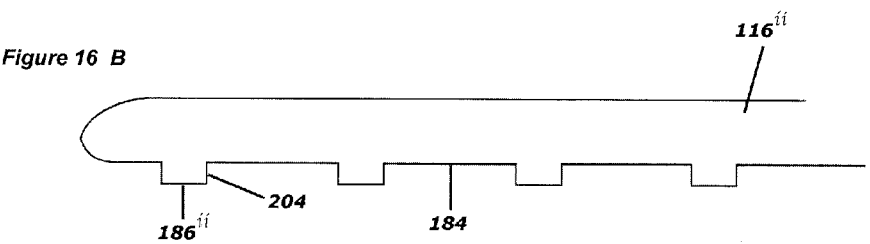
Figure 16:
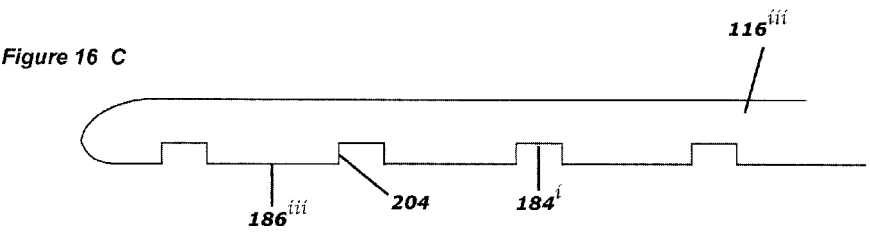
Figure 16:
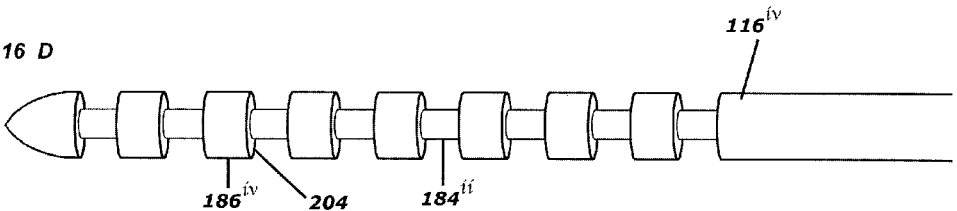

In the embodiment shown in FIG. 16A, the distal end 116 includes protrusions 186$^i$ that extend out beyond the outer diameter of the distal end 116$^i$ of the rod 102.

In the embodiment shown in FIG. 16B, the distal end 116$^{ii}$ includes protrusions 186$^{ii}$ that are not curved on their distal aspect but still have a surface 204 to abut the distal screw 108.

In the embodiment shown in FIG. 16C, the distal end 116$^{iii}$ includes protrusions 186$^{iii}$ that are flat and long relative to protrusions 186, and further includes relatively short recesses 184' for capturing a distal screw 108 to allow compression at the fracture site.

In the embodiment shown in FIG. 16D, the distal end 116$^{iv}$ includes circumfrential protrusions 186$^{iv}$ and recesses 184" with a surface 204 to abut the edge of a distal screw 108.

Although the preceding description details the use of the compression rod 102 in the ulna, there are other applications within the scope of the invention. For example, the rod 102 could be used in a nearly identical manner in other long bones with an intramedullary canal, including, but not limited to, the radius, humerus, tibia, fibula, femur, clavicle, metacarpal, or phalanx. The device 100 is demonstrated with a mid-shaft fracture, but it could be used with fractures at locations all along the bone with the exception of fractures at locations corresponding to the distal end of the rod 102. The rod 102 could also be used as a minimally invasive fixation for ulnar shortening osteotomies or other long bone osteotomies.

A selected illustrative embodiment of the invention is described above in some detail. It should be understood that only structures considered necessary for clarifying the present invention have been described herein. Other conventional structures, and those of ancillary and auxiliary components of the system, are assumed to be known and understood by those skilled in the art. Moreover, while a working example of the present invention has been described above, the present invention is not limited to the working example described above, but various design alterations may be carried out without departing from the present invention as set forth in the following claims.

What is claimed is:

1. An apparatus for use in stabilizing a fracture of a bone, the apparatus comprising an intermedullary device, wherein the intermedullary device comprises a rod having a longitudinal axis and including an insertion end and a proximal end opposed to the insertion end, wherein the rod includes a first cross-sectional dimension at the proximal end and second cross-sectional dimension at the insertion end, the second cross-sectional dimension being less than the first cross-sectional dimension, the rod further including:
   a first through-hole at the proximal end of the rod and configured to receive a first interlock screw to maintain proximal and distal positioning of the rod;
   a plurality of recesses formed along an outer surface of the insertion end of the rod in a direction transverse to the axis, each recess including a flat engaging surface extending substantially transverse to the axis, a curved surface longitudinally spaced apart along the axis from the engaging surface, and a sliding surface extending between the engaging surface and the curved surface in a direction parallel to the axis, and
   a jig interface, at the proximal end of the rod, including a protuberance, in cross section, having a non-circular shape and a hole configured to receive an alignment jig.

2. The apparatus of claim 1 wherein the sliding surface is flat.

3. The apparatus of claim 1 further comprising a rod engaging member including a first surface configured to engage a respective one of the plurality of sliding surfaces of the rod, and a second surface configured to engage a respective one of the plurality of engaging surfaces of the rod.

4. The apparatus of claim 1 wherein the jig interface is configured to permit connection of the rod to a second device.

5. The apparatus of claim 4 wherein the jig interface is configured to permit connection of the rod to the second device in such a way that rotation of the rod relative to the second device is prevented.

6. The apparatus a claim 1 wherein at least a portion of the rod is tapered.

7. The apparatus of claim 1, wherein each recess is elongate such that the dimension parallel to the longitudinal axis of the rod is greater than the dimension transverse to the longitudinal axis of the rod.

8. The apparatus of claim 1, wherein the curved surface faces the insertion end of the rod.

9. The apparatus of claim 3, wherein the rod engaging member comprises a headless screw.

10. The apparatus of claim 1, wherein the rod includes a midpoint between the insertion end and the proximal end, and the recesses are disposed between the insertion end and the midpoint.

11. The apparatus of claim 1, wherein the corresponding first interlock screw is configured to simultaneously engage bone on transversely opposed sides of the rod when received in the first through hole.

12. The apparatus of claim 11, further comprising a second through hole configured to receive a second interlock screw, the second through hole extending transverse to the longitudinal axis and at an angle to the first through hole.

13. The apparatus of claim 1, wherein the intramedullary device further comprises a compression generating device configured to engage the proximal end of the rod and axially move the rod relative to the bone.

* * * * *